United States Patent [19]

Newkome

[11] Patent Number: 4,598,073
[45] Date of Patent: Jul. 1, 1986

[54] CERTAIN POLYCYCLO-PALLADIUM-BIPYRIDINE COMPLEXES HAVING ANTI-TUMOR ACTIVITY

[75] Inventor: George R. Newkome, Baton Rouge, La.

[73] Assignee: Research Corporation, New York, N.Y.

[21] Appl. No.: 518,672

[22] Filed: Jul. 29, 1983

Related U.S. Application Data

[63] Continuation-in-part of Ser. No. 447,109, Dec. 6, 1982, abandoned, which is a continuation of Ser. No. 276,047, Jun. 22, 1981, abandoned, which is a continuation of Ser. No. 141,318, Apr. 18, 1980, abandoned.

[51] Int. Cl.$^4$ .................. C07F 7/00; A61K 31/28
[52] U.S. Cl. ................................. 514/185; 514/492; 546/10
[58] Field of Search .............. 546/2, 10, 88; 424/131; 514/185, 492

[56] References Cited

PUBLICATIONS

Newkome et al. (I), Journal of the American Chemical Society, vol. 102, No. 13, pp. 4551–4552, pub. Jun. 18, 1980.
Newkome et al., (II), Journal of the American Chemical Society, vol. 103, No. 12, pp. 3423–3429, pub. Jun. 17, 1981.

*Primary Examiner*—Alan L. Rotman
*Attorney, Agent, or Firm*—Scully, Scott, Murphy & Presser

[57] ABSTRACT

The invention relates to novel palladium complexes of the formulae:

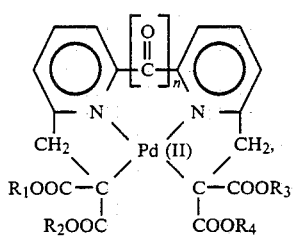

(I)

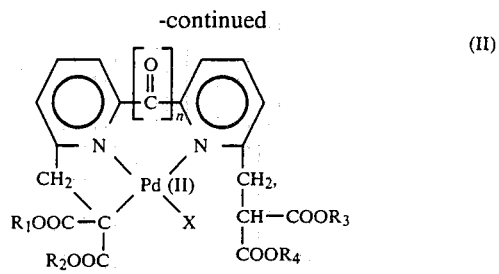

(II)

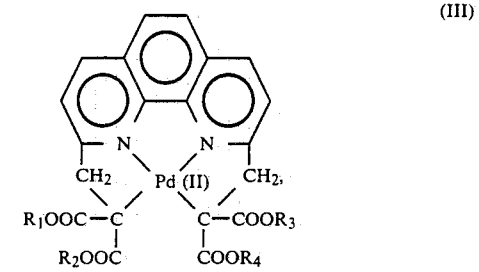

(III)

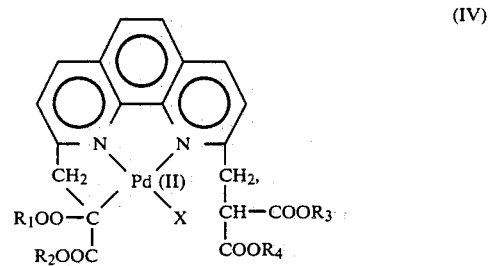

(IV)

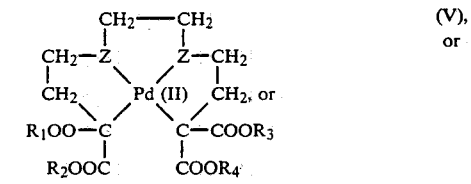

(V), or

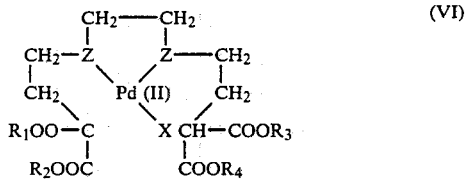
(VI)

wherein:
n is 0 or 1,
$R_1$, $R_2$, $R_3$, $R_4$ are lower alkyl groups, fluoro substituted lower alkyl groups, or (lower) alkyl, or

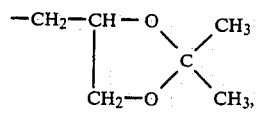

X is a monovalent anionic ligand, and
Z is O, S, P or $NR_1$, and anti-tumor pharmaceutical compositions and therapeutic methods of treating tumors employing the palladium complexes.

22 Claims, No Drawings

CERTAIN POLYCYCLO-PALLADIUM-BIPYRIDINE COMPLEXES HAVING ANTI-TUMOR ACTIVITY

CROSS-REFERENCE TO RELATED APPLICATIONS

This application is a continuation-in-part of application Ser. No. 447,109, filed Dec. 6, 1982, now abandoned, which application, in turn, is a continuation of application Ser. No. 276,047, filed June 22, 1981, now abandoned, which application, in turn, is a continuation of application Ser. No. 141,318, filed Apr. 18, 1980, now abandoned.

BACKGROUND OF THE INVENTION

The present invention relates to novel palladium coordination complexes and their use in the treatment of animal tumors.

Recently, certain platinum complexes have been shown by Rosenberg and co-workers to be highly active anti-tumor agents (U.S. Pat. Nos. 4,177,263 and 4,140,707). For example, the complex cis-dichlorodiammine-platinum-II is the chemotherapeutic agent of choice in the treatment of many and varied tumors.

There are several drawbacks, however, associated with the use of the platinum complexes to treat tumors. Generally, the platinum complexes have a relatively low solubility in water thereby rendering it difficult to formulate a composition which can effectively deliver the reagent to the site of the tumor in the body.

Moreover, many of the platinum complexes are highly nephrotoxic thereby further restricting their use, in the absence of precautionary measures to avoid damage to the kidneys, when administered to animals afflicted with tumors.

Additionally, platinum complexes and cis-dichlorodiammine-platinum-II in particular are relatively inactive against gastro-intestinal tumors, presumably because of an inability of the complex to aquate in the presence of the high chloride concentrations found in the stomach.

It has previously been suggested to employ certain palladium complexes as anti-tumor agents in chemotherapy. However, in all instances reported in the literature the complexes tested had either little or marginal anti-tumor activity. The low activity of the palladium complexes tested heretofore, as compared with related palladium complexes, has been attributed to the fast acuation of the leaving groups which disassociate from the metal in vivo. See Connors, *Cancer Treatment Reports,* Vol. 63, September–October, 1979, pages 1499–1502; Lim et al., *J. Inorg. Nucl. Chem.,* Vol. 38, pages 1911–1914 (1976); Connors, Platinum Cooridination Complexes in Cancer Chemotherapy, pages 13–37 (Springer-Verlag Berlin, 1974); Cleare, *Bioinorganic Chemistry,* Vol. 2, pages 187–210 (1973); Graham et al, *J. Inorg. Nucl. Chem.,* Vol. 41, pages 1245–1249 (1979); Kirschner et al, *J. Med. Chem.,* Vol. 9, pages 369–372 (1966); Kirschner et al, 168*th Annual. Meet.,* ACS (September, 1974) (abstract); Kirschner et al, Adv. Exp. Med. Biol., Vol. 91, 151 (1977); Kirschner et al, *Inorganic and Nutritional Aspects of Cancer,* pages 151–160, Plenum, N.Y. (1978); Kirschner et al, *J. Clin. Hema. and Omc.,* Vol. 7, page 190 (1977).

It is an object of the present invention to provide novel palladium coordination complexes having a high degree of anti-tumor activity which do not possess the disadvantageous characteristics associated with known heavy metal chemotherapeutic anti-tumor agents and with platinum complexes in particular.

It is a further object of the present invention to provide a pharmaceutical composition comprising the novel palladium complexes especially adapted for the treatment of animal tumor cells sensitive thereto.

It is a further object of the present invention to provide a therapeutic method for the treatment of animals afflicted with tumors sensitive to the novel palladium complexes.

SUMMARY OF THE INVENTION

The present invention provides novel palladium coordination complexes having the formulas:

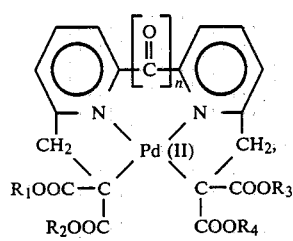
(I)

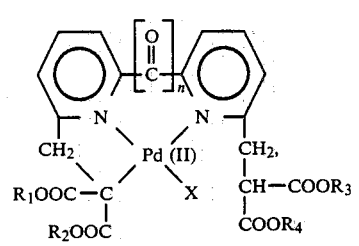
(II)

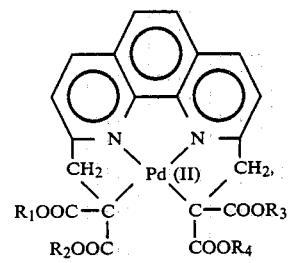
(III)

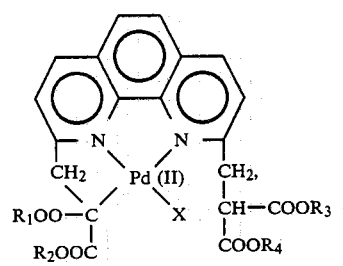
(IV)

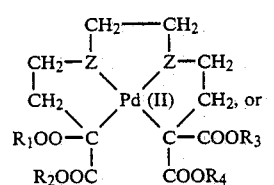
(V)

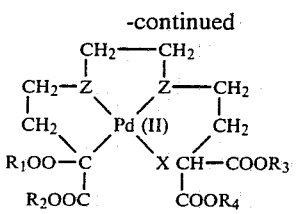

wherein:

n is 0 or 1,

R$_1$, R$_2$, R$_3$, R$_4$ are lower alkyl groups, fluoro substituted lower alkyl groups, or (lower) alkyl, or

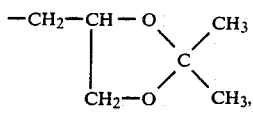

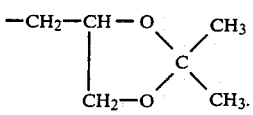

X is a monovalent anionic ligand, and

Z is O, S, P or NR$_1$.

The present invention also provides pharmaceutical compositions in unit dosage form especially adapted for the treatment of animal tumor cells sensitive to the palladium complexes of formulas (I) through (VI) above comprising a pharmaceutically acceptable carrier and an anti-tumor effective amount of a palladium coordination complex of either of formulas (I) through (VI).

The present invention additionally provides a therapeutic method for the treatment of animal tumors comprising administering to an animal afflicted with tumor cells sensitive to the palladium complexes of formulas (I) through (VI) an anti-tumor effective amount of a palladium coordination complex of either of formulas (I) through (VI).

DETAILED DESCRIPTION OF THE INVENTION

In the above formulas (I) through (VI), all references to "lower alkyl" groups are to n- and isoalkyl groups having from 1 to 10 carbon atoms.

Especially preferred lower alkyl groups are methyl, ethyl, isopropyl, and t-butyl. Preferred among the ar(-lower)alkyl groups is benzyl. The preferred fluoro-substituted lower alkyl group is CF$_3$—CH$_2$—.

In the said formulas (I) through (VI), X may be any pharmaceutically acceptable anionic monovalent ligand, such as Cl, Br, SCN, NO$_3$, CH$_3$CO$_2$, etc. The preferred monovalent anionic ligand is Cl.

The anti-tumor palladium complexes of the invention may be administered orally or by intraperitoneal injection to an animal afflicted with tumor cells sensitive thereto. The preferred mode of administration is by inraperitoneal injection.

The palladium complexes of the invention may be formulated into pharmaceutical compositions according to conventional techniques employing any pharmaceutically acceptable carrier which is inert with respect thereto.

Suitable carriers include:

Conventional methods for formulation or compounding the palladium complexes with the carriers to produce the pharmaceutical compositions in unit dosage form are described in Roberts et al, Carnegie Institute, Wash. Pub. 60F, 5 (1955).

Pharmaceutical carriers may include water, saline, buffer or ethanolic solutions and may be injected as a solution. Oral tablets are prepared according to conventional methods and coated, if desired. The preferred tablet preparations are those that compound the complexes in a time-released formulation such as described by Sheth et al, U.S. Pat. No. 4,140,755. Suitable carriers for use in tablets include hydroxypropylmethylcellulose anionic or nonionic hydrophillic gums, modified cellulosic substances or proteinaceous materials such as: acacia, gum tragacanth, locust bean gum, agar, pectin, et cetera; the preferred carrier being hydroxypropylmethylcellulose.

The amount of palladium complex to be included in each unit dosage form of the pharmaceutical composition will depend, as will be understood by those skilled in the art, on the particular complex employed, its degree of anti-tumor activity and toxicity. Relatively greater amounts of the less active and less toxic complexes will be required to affect the growth of tumors whereas relatively lesser of the more active and more toxic complexes will be required to similarly affect tumor growth. Generally, amounts in the range of from 2 to 400 mg, preferably from 2 to 200 mg, may be included in each unit dosage form of the pharmaceutical composition.

The dosage of anti-tumor palladium complex administered will depend in each case upon a variety of factors including the nature of the tumor and animal undergoing treatment, the activity and toxicity of the particular palladium complex employed, et cetera. Generally, however, dosages in the range of from 2 to 400 mg/kg of body weight of the animal treated, preferably from 2 to 200 mg/kg are sufficient to effect a regression of the tumor.

The palladium complexes of the invention also find utility as homogeneous catalysts, heterogeneous catalysts, and intermediates in organic synthesis.

The complexes, in the presence of a reductive environment, may successfully be used to reduce alkenes and alkynes, when R$_1$ to R$_4$ are larger than ethyl (C$_2$). Incorporation of these organometallics within a polymer backbone afford heterogeneous catalysts also capable of reducing olefins in a hydrogen atmosphere. When R$_1$ to R$_4$ are smaller than ethyl, these complexes may be used as synthetic intermediates or for the chemical deposition of palladium under reductive conditions.

The palladium complexes of the invention may be prepared according to the following methods:

Complexes of formulas I and II may be prepared by reacting the appropriate bis[bis(alkoxycarbonyl)ethyl]-dipyridine with a palladating reagent, preferably in the presence of a basic catalyst. According to one method a solution of an alkali metal alkoxide in absolute alcohol is added dropwise to an anhydrous organic solvent solution of PdCl$_2$(PhCN)$_2$ or Na$_2$PdCl$_4$ and the bis[bis(alkoxycarbonyl)ethyl]dipyridine and the palladium complex product isolated from the reaction mixture.

In an alternative method anhydrous K$_2$CO$_3$ is added to a mixture of Na$_2$PdCl$_4$ or other alkali metal palladous chloride or PdCl$_2$ and the bis[bis(alkoxycarbonyl)ethyl]dipyridine in an anhydrous organic solvent and the desired product isolated following the completion of the reaction.

The bis[bis(alkoxycarbonyl)ethyl]-dipyridine intermediates for the above reactions are conveniently prepared by reacting an appropriate malonate ester with a bis-(chloromethyl)dipyridine in the presence of an HCl scavenger, preferably in an inert organic solvent.

Complexes of formulas III and IV may be prepared by reacting the appropriate bis[bis(alkoxycarbonyl)ethyl]phenanthroline and a palladating agent such as $PdCl_2$ in an anhydrous organic solvent solution in the presence of an HCl scavenger. The desired product is easily isolated from the reaction mixture.

The intermediate phenanthroline derivative may be prepared by reacting an appropriate malonate ester with a bis-(chloromethyl)phenanthroline in the presence of an HCl scavenger, preferably in an inert organic solvent.

Palladium complexes of formulas V or VI may be prepared by reacting a palladating agent such as $PdCl_2$ with an appropriate bis[bis(alkoxycarbonyl)propoxy]ethane in an inert organic solvent followed by isolation of the final product from the reaction mixture.

The intermediate ether is conveniently prepared by reacting an appropriate malonate with a bis(chloroethoxy)ethane in an inert organic solvent in the presence of an HCl scavenger.

The invention is illustrated by the following non-limiting examples.

EXAMPLE 1

6,6'-Bis[1'',1'''-bis(methoxycarbonyl)ethyl]-2,2'-dipyridine

A mixture of 0.04 mol of dimethyl malonate, 0.01 mol of 6,6'-bis(chloromethyl)-2,2'-dipyridine and 0.035 mol of anhydrous $K_2CO_3$ was stirred in 25 mL of N,N-dimethylformamide at 25° C. for 24 hours. The mixture was filtered and concentrated in vacuo to give a light yellow viscous oil, which was dissolved in $CH_2Cl_2$, purified through a silica gel column, concentrated in vacuo and purified by thick layer chromatography on silica gel. The product was recrystallized from $CH_2Cl_2/C_6H_{12}$: 95%, mp 138°–140° C.; $^1H$ NMR (CDCl$_3$; 200 MHz) δ 3.50 (d, PyCH$_2$, J=7.5 Hz, 4H), 3.74 (s, OCH$_3$, 12H), 4.29 (t, CH(CO$_2$Me)$_2$, J=7.5 Hz, 2H), 7.19 (d, 5-PyH, J=8.0 Hz, 2H), 7.70 (t, 4-PyH, J=8.0 Hz, 2H), 8.26 (d, 3-PyH, J=8.0 Hz, 2H); $^{13}C$ NMR (CDCl$_3$) δ 35.73 (PyCH$_2$), 49.99 [CH(CO$_2$Me)$_2$], 52.21 (CH$_3$O), 118.40 (C3), 122.88 (C5), 136.88 (C4), 155.03 (C6), 156.43 (C2), 169.48 (C=O); IR (KBr) 1735 (C=O), 1570, 1435, 1280, 1235 cm$^{-1}$; MS (70 eV) m/e 444 (M+, 23), 385 (M+—C$_2$H$_3$O$_2$, 82), 381 (C$_{20}$H$_{17}$N$_2$O$_6$+, 37), 327 (M+—C$_4$H$_5$O$_4$, 25), 321 (C$_{18}$H$_{13}$N$_2$O$_4$, 100).

Anal. Calcd. for $C_{22}H_{24}N_2O_8$: C, 59.45; H, 5.44; N, 6.30. Found: C, 59.22; H, 5.52; N, 6.26.

EXAMPLE 2

6,6'-Bis[1'',1'''-bis(ethoxycarbonyl)ethyl]-2,2'-dipyridine

The intermediate was prepared according to the method of Example 1 to yield crystalline solid, which was recrystallized from $CH_2Cl_2/C_6H_{12}$: 90%; mp 55°–56° C.; $^1H$ NMR (CH$_2$Cl$_2$; 200 MHz) δ 1.22 (t, CH$_2$CH$_3$, J=7.3 Hz, 12H), 3.45 (d, PyCH$_2$, J=7.7 Hz, 4H), 4.15 (q, CH$_2$CH$_3$, J=7.3 Hz, 8H), 4.22 [t, CH(CO$_2$Et)$_2$, J=7.7 Hz, 4H], 7.18 (d, 5-pyH, J=7.7 Hz, 2H), 7.77 (t, 4-pyH, J=7.7 Hz, 2H), 8.24 (d, 3-PyH, J=7.7 Hz, 2H); $^{13}C$ NMR (CDCl$_3$) δ 13.78 (CH$_2$CH$_3$), 35.77 (PyCH$_2$), 50.40 [CH(CO$_2$Et)$_2$], 61.04 (CH$_2$CH$_3$), 118.47 (C3), 122.93 (C5), 136.78 (C4), 155.01 (C6), 156.57 (C2), 169.09 (C=O); IR (KBr) 1742, 1726 (C=O), 1584, 1574, 1473 (C—O), 1447 cm$^{-1}$; MS (70 eV) m/e 500 (M+, 17), 455 (M+—C$_2$H$_5$O, 25), 427 (M+—C$_3$H$_5$O$_2$, 70), 335 (100).

Anal. Calcd. for $C_{26}H_{32}N_2O_8$; C, 62.39; H, 6.44; N, 5.60. Found: C, 62.42; H, 6.48; N, 5.43.

EXAMPLE 3

6,6'-Bis[1'',1'''-bis(isopropoxycarbonyl)ethyl]-2,2'-dipyridine

The intermediate was prepared according to the method of Example 1 to yield a white crystalline solid, which was recrystallized from Et$_2$O/petroleum ether (bp 30°–60° C.): 90%, mp 73°–74° C.; $^1H$ NMR (CDCl$_3$; 200 MHz) δ 1.20 [d, CH(CH$_3$)$_2$, J=4.1 Hz, 24H], 3.47 (d, PyCH$_2$, J=7.5 Hz, 4H), 4.24 [t, CH(CO$_2$R)$_2$, J=7.5 Hz, 2H], 5.04 [h, CH(CH$_3$)$_2$, J=6.5 Hz, 4H], 7.18 (d, 5-PyH, J=7.5 Hz, 2H), 7.69 (t, 4-PyH, J=7.5 Hz, 2H), 8.29 (d, 3-PyH, J=7.5 Hz, 2H); $^{13}C$ NMR (CDCl$_3$) δ 21.39 [CH(CH$_3$)$_2$], 35.72 (PyCH$_2$), 50.72 [CH(CO$_2$R)$_2$], 68.47 [CH(CH$_3$)$_2$], 118.53 (C3), 122.95 (C5), 136.69 (C4), 155.00 (C6), 156.72 (C2), 168.67 (C=O); IR (KBr) 1725 (C=O), 1570, 1270, 1180, 1150 cm$^{-1}$; MS (70 eV) m/e 556 (M+, 10), 469, 383, 349, 263, 209 (100), 43 (C$_3$H$_7$+, 72).

Anal. Calcd. for $C_{30}H_{40}N_2O_8$: C, 64.73; H, 7.24; N, 5.03. Found: 64.81; H, 7.11; N, 5.02.

EXAMPLE 4

6,6'-Bis[1'',1'''-bis(tert-butoxycarbonyl)ethyl]-2,2'-dipyridine

The intermediate was prepared according to Example 1 to yield a white crystalline solid, which was recrystallized from CHCl$_3$/C$_6$H$_{12}$ (1:9): 90%, mp 109°–110° C.; $^1H$ NMR (CDCl$_3$; 200 MHz) δ 1.40 [s, C(CH$_3$)$_3$, 36H], 3.39 (d, PyCH$_2$, J=7.9 Hz, 4H), 4.13 (t, CH(CO$_2$R)$_2$, J=7.9 Hz, 2H), 7.17 (d, 5-PyH, J=7.9 Hz, 2H), 7.65 (t, 4-PyH, J=7.9 Hz, 2H), 8.34 (d, 3-PyH, J=7.9 Hz, 2H), $^{13}C$ NMR (CDCl$_3$) δ 27.49 [C(CH$_3$)$_3$], 35.87 (PyCH$_2$), 52.15 [CH(CO$_2$R)$_2$], 80.75 [C(CH$_3$)$_3$], 118.39 (C 3), 122.83 (C5), 136.47 (C4), 154.81 (C6), 156.94 (C2), 168.30 (C=O); IR (KBr) 2975 (C—H), 1720 (b, C=O); MS (70 eV) m/e 612 (M+, 5), 343 (61), 281 (51), 209 (57), 57 (C$_4$H$_9$+, 100).

Anal. Calcd. for $C_{34}H_{48}N_2O_8$: C, 66.64; H, 7.90; N, 4.57. Found: C, 66.46; H, 7.80; N, 4.46.

EXAMPLE 5

6,6'-Bis[1'',1'''-bis(benzyloxycarbonyl)ethyl]-2,2'-dipyridine

The intermediate was prepared according to the method of Example 1 to yield a white crystalline solid, which was recrystallized from CHCl$_3$/C$_6$H$_{12}$: 85%; mp 87°–88° C.; $^1H$ NMR (CDCl$_3$, 200 MHz) δ 3.45 (d, PyCH$_2$, J=7.3 Hz, 4H), 4.45 [t, CH(CO$_2$R)$_2$, J=7.6 Hz, 2H], 5.14 (m, OCH$_2$Ph, 8H), 7.12 (d, 5-PyH, J=7.9 Hz, 2H), 7.26 (m, OCH$_2$Ph, 20H), 7.52 (t, 4-PyH, J=7.9 Hz, 2H), 8.20 (d, 3-PyH, J=7.9 Hz, 2H); $^{13}C$ NMR (CDCl$_3$) δ 35.84 (PyCH$_2$), 50.40 [CH(CO$_2$R)$_2$], 67.06 (OCH$_2$Ph), 118.78 (C3) 123.01 (C5), 127.94–128.41 (C'2, 3, 4, 5, 6), 135.37 (C'1), 137.01 (C4), 155.09 (C6), 156.34 (C2), 169.09 (C=O); IR (KBr) 1740, 1720 (C=O); MS (70 eV) m/e 108 (87), 91 (70), 79 (100), 77 (74).

Anal. Calcd. for $C_{46}H_{40}N_2O_8$: C, 73.78; H, 5.38; N, 3.74. Found: C, 73.79; H, 5.42; N, 3.54.

EXAMPLE 6

6,6'-Bis[1",1"-bis(methoxycarbonyl)ethyl]-2,2'-dipyridine-Palladium(II)

The product was prepared by adding a solution of 8 mmol of sodium ethoxide in 5 ml of absolute ethanol dropwise to an anhydrous THF solution of $PdCl_2(PhCN)_2$ (3.3 mmol) and 3 mmol of the intermediate of Example 1. The mixture was stirred for 24 hours at 25° C. and concentrated in vacuo to give the crude complex, which was recrystallized from $CHCl_3/C_6H_{12}$ to yield the pure palladium complex (48%) as a yellow powder: mp 178°-182° C. (dec); $^1$H NMR $(CDCl_3)$ δ 3.77 (s, $OCH_3$, 12H), 4.02 (s, $PyCH_2$, 4H), 7.50 (d, 5-PyH, J=8.0 Hz, 2H), 7.62 (d, 3-PyH, J=8.0 Hz, 2H), 7.89 (t, 4-PyH, J=8.0 Hz, 2H); IR (KBr) 1730 (C=O), 1290, 1190, 1065 cm$^{-1}$; MS (70 eV) m/e 548 (M$^+$, 5) 547 (M$^+$—1, 5), 357, 325, 321, 293 (100).

Anal. Calcd. for $C_{22}H_{22}N_2O_8Pd$: C, 48.15; H, 4.04; N, 5.10. Found: C, 48.18; H, 4.25; N, 4.99.

EXAMPLE 7

Chloro[6,6'-Bis[1",1"-bis(methoxycarbonyl)ethyl]-2,2'-dipyridine]Palladium(II)

The chloro complex is an intermediate, which was not isolated, in the preparation of the organometallic described in Example 6. If the reaction time is limited or 1 equiv. of base is utilized, this intermediate can be isolated. The detection via NMR spectroscopy confirms its intermediacy. [The NMR is identical to that of Example 9, except for the two singlet at δ 3.74 and 3.79 for the OMe group replacing the ethyl moieties.]

EXAMPLE 8

6,6'-Bis[1",1"-bis[(ethoxycarbonyl)ethyl]-2,2'-dipyridine]Palladium(II)

A solution of sodium ethoxide (1 mmol), in absolute ethanol (1.6 ml) was added dropwise to a THF solution of $PdCl_2(PhCN)_2$ (140 mg, 0.36 mmol) and the bismalonate ligand 6,6'-bis-(ethoxycarbonyl)ethyl 2,2'-dipyridine (170 mg, 0.34 mmol). The mixture was stirred for 12 hours at 25° C., then concentrated in vacuo to give a solid, which was recrystallized from benzene and diethyl ether affording the stable cis-organometallic complex, which based on spectral data contains two cis-palladium-carbon bonds making up a novel (5.5.5) fused ring system with a pivotal metal ion: 51 mg (25%); mp 220°-222° C. (dec, in air); NMR $(CD_2Cl_2;$ 200 MHz) δ 1.21 (t, J=7.2 Hz, $CH_2CH_3$, 12H), 3.90 (s, Pyr—$CH_2$, 4H), 4.14 (m, $CH_2CH_3$, 8H), 7.49 (d, J=7.8 Hz, 5-PyH, 2H), 7.64 (d, J=7.8 Hz, 3-PyH, 2H), 7.91 (t, J=7.8 Hz, 4-PyH, 2H);

IR (KBr) 1730, (C=O), 1603, 1570, 1474, 1446 cm$^{-1}$; MS (70 eV) m/e 606 (M$^{108}$Pd, 2.4), 603 (M$^{105}$Pd, 2.04). 561 (558 and 559) (M$^+$—OEt, 1.2), 205 (100).

Anal. Calcd. for $C_{26}H_{30}N_2O_8Pd$ (MW 604.93); C, 51.62; H, 5.00; N, 4.63. Found: C, 51.65, H, 5.05; N, 4.60.

In addition, mass spectrum of this compound exhibited a parent-ion isotope pattern centered at m/e 604 in accord with the proposed structure.

The complex was also prepared by stirring the starting ligand, $Li_2PdCl_4$, and $K_2CO_3$ in acetonitrile to give the identical cis-Pd organometallic product.

In order to increase the yield to 100% of the title compound, chloro[6,6'-bis-[(1",1"-bis(ethoxycarbonyl)ethyl)]-2,2'-dipyridine]palladium(II) [prepared as an intermediate in this procedure-Example 9] was treated with $AgNO_3$ and $K_2CO_3$ in acetonitrile at 25° C. for 1 hour. The product of this procedure is identical in all respects to the above. The absence of $K_2CO_3$ resulted in not forming the C-Pd bond, even though $AgNO_3$ was present.

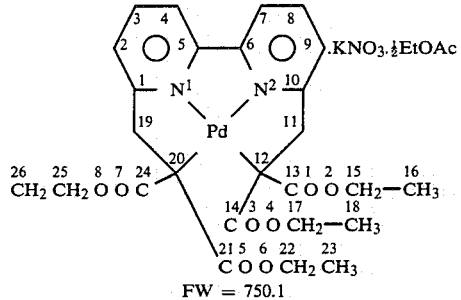

FW = 750.1

| | Monoclinic, C2/c | | Z = 8 | | MoK$_2$ radiation | | |
|---|---|---|---|---|---|---|---|
| | a = 20.161(4) | | $d_c$ = 1.616 gcm$^{-3}$ | | μ = 7.924 cm$^{-1}$ | | |
| | b = 17.991(4) | | R = 0.074 | | | | |
| | c = 17.995(3)Å | | for 1897 observations | | | | |
| | β = 109.16(2)° | | & 183 variables | | | | |

X-Ray Data

| Atom | x | y | z | B.Å$^2$ | Atom | x | y | z | B.Å$^2$ |
|---|---|---|---|---|---|---|---|---|---|
| Pd | 0.84892(7) | 0.01446(7) | 0.17569(7) | 2.43(2) | C9 | 0.8291(9) | −0.2078(10) | 0.2349(10) | 3.9(4) |
| 01 | 0.6681(5) | 0.0299(6) | 0.0905(6) | 3.9(3) | C10 | 0.8229(8) | −0.1301(9) | 0.2294(9) | 2.9(4) |
| 02 | 0.7004(6) | −0.0892(7) | 0.1096(6) | 4.0(3) | C11 | 0.7757(8) | −0.0808(10) | 0.2581(9) | 3.3(4) |
| 03 | 0.7009(6) | 0.1040(7) | 0.2336(6) | 4.2(3) | C12 | 0.7578(7) | −0.0057(9) | 0.2107(8) | 2.6(3) |
| 04 | 0.7831(5) | 0.0527(6) | 0.3325(6) | 3.3(2) | C13 | 0.7046(8) | −0.0176(10) | 0.1338(9) | 3.4(3) |
| 05 | 0.8938(7) | 0.1956(8) | 0.2468(7) | 5.4(3) | C14 | 0.7429(8) | 0.0552(9) | 0.2560(9) | 2.8(3) |
| 06 | 0.7817(6) | 0.2062(7) | 0.1740(7) | 4.4(3) | C15 | 0.6533(9) | −0.1048(11) | 0.0299(10) | 4.3(4) |
| 07 | 0.8391(6) | 0.0983(7) | −0.0020(7) | 4.6(3) | C16 | 0.6647(11) | −0.1859(12) | 0.0149(12) | 5.6(5) |
| 08 | 0.7487(6) | 0.1450(6) | 0.0277(6) | 3.8(3) | C17 | 0.7701(9) | 0.01084(10) | 0.3839(10) | 3.9(4) |

| | | | | | | | | |
|---|---|---|---|---|---|---|---|---|
| N1 | 0.9350(6) | −0.0020(7) | 0.1474(6) | 2.2(2) | C18 | 0.8200(10) | 0.0974(11) | 0.4650(10) | 4.5(4) |
| N2 | 0.8647(6) | −0.0929(7) | 0.1984(7) | 2.4(3) | C19 | 0.9370(9) | 0.1303(10) | 0.1380(10) | 3.5(4) |
| C1 | 0.9673(8) | 0.0555(9) | 0.1272(9) | 2.5(3) | C20 | 0.8596(8) | 0.1242(9) | 0.1340(9) | 2.8(3) |
| C2 | 1.0262(9) | 0.0409(10) | 0.1032(10) | 3.9(4) | C21 | 0.8370(8) | 0.1782(9) | 0.1832(9) | 3.4(4) |
| C3 | 1.0449(9) | −0.0306(10) | 0.1009(10) | 3.9(4) | C22 | 0.8847(11) | 0.2488(13) | 0.3043(12) | 5.7(5) |
| C4 | 1.0126(8) | −0.0895(9) | 0.1215(9) | 3.0(4) | C23 | 0.9291(13) | 0.3132(14) | 0.3070(14) | 7.3(6) |
| C5 | 0.9547(7) | −0.0727(8) | 0.1463(8) | 2.2(3) | C24 | 0.8142(8) | 0.1211(10) | 0.0481(9) | 3.3(4) |
| C6 | 0.9136(8) | −0.1263(9) | 0.1747(9) | 2.8(3) | C25 | 0.7084(11) | 0.1515(12) | −0.0571(12) | 5.7(5) |
| C7 | 0.9209(9) | −0.2029(10) | 0.1788(10) | 3.5(4) | C26 | 0.6748(13) | 0.0813(14) | −0.0865(14) | 7.4(6) |
| C8 | 0.8763(9) | −0.2448(10) | 0.2088(10) | 3.8(4) | | | | | |
| K | 0.3326(4) | 0.1585(4) | 0.3940(4) | 9.8(2) | O2S* | 0.5540(26) | 0.0839(29) | 0.3342(29) | 14.3(16) |
| O1A | 0.4351(9) | 0.2338(10) | 0.3975(10) | 8.7(5) | N1A | 0.4604(9) | 0.237(1) | 0.469(1) | 5.8(4) |
| O2A | 0.5108(8) | 0.2743(9) | 0.5005(9) | 6.9(4) | C1S | 0.496(3) | 0.055(3) | 0.320(3) | 20.(2) |
| O3A | 0.4256(10) | 0.2074(12) | 0.5068(12) | 10.9(6) | C2S | 0.489(2) | 0.020(2) | 0.378(2) | 13.(1) |
| O1S | 0.5 | 0.0242(22) | 0.25 | 14.7(11) | | | | | |

Estimated standard deviations in the least significant digits are shown in parentheses
*Population = ½.

EXAMPLE 9

Chloro[6,6'-Bis[1",1"-(bis(ethoxycarbonyl)ethyl]-2,2'-dipyridine]Palladium(II)

The method of preparation was the same as Example 8 except that the intermediate was isolated:
mp 187°–189° C. (dec); $^1$N NMR (CD$_2$Cl$_2$) δ 1.18 (t, CH$_2$C$\underline{H}_3$, J=7.3 Hz, 6H), 1.26 (t, CH$_2$C$\underline{H}_3$, J=7.3 Hz, 6H), 3.59 (s, PyC$\underline{H}_2$, 2H), 3.93 (d, PyC$\underline{H}_2$CH, J=7.8 Hz, 2H), 4.11 (dq, C$\underline{H}$(CO$_2$CH$_2$CH$_3$)$_2$, J=7.1, 1.0 Hz, 4H), 4.15 (dq, PdC(CO$_2$CH$_2$C$\underline{H}_3$)$_2$, J=7.1, 1.0 Hz, 4H), 4.25, 4.29 (2d, PyC$\underline{H}_2$C$\underline{H}$, J=8.5, 8.5 Hz, 1H), 7.39 (dd, 5'-Py$\underline{H}$, J$_{5',4'}$=6.4, J$_{5',3'}$=2.7 Hz, 1H), 7.54 (dd, 5-Py$\underline{H}$, J$_{5,4}$=7.8, J$_{5,3}$=1.0 Hz, 1H), 7.77 (dd, 3-Py$\underline{H}$, J$_{3,4}$=7.6, J$_{3,5}$=1.0 Hz, 1H), 7.90 (dd, 3'-Py$\underline{H}$, J$_{3',4'}$=5.9, J$_{3',5}$=1.5 Hz, 1H), 7.91 (t, 4-Py$\underline{H}$, J=7.9 Hz, 1H), 7.96 (t, 4'-Py$\underline{H}$, J=8.0 Hz, 1H); IR (KBr) 1728, 1604, 1573, 1473, 1445 cm$^{-1}$.

EXAMPLE 10

Chloro[6,6'-Bis[1",1"-bis(isopropoxycarbonyl)ethyl]-2,2'-dipyridine]Palladium(II)

The complex was prepared by stirring a mixture of 2.0 mmol of PdCl$_2$ and 1.9 mmol of 6,6'-bis[1",1"-bis(isopropoxycarbonyl)ethyl]-2,2'-dipyridine in 20 ml of anhydrous acetonitrile for 1 hour at 50° C. K$_2$CO$_3$ (100 mg) was added to the cooled reaction mixture and stirred for 24 hours at 55° C. under a nitrogen atmosphere. The heterogeneous reaction mixture was filtered through celite, concentrated in vacuo and the crude product dissolved in CH$_2$Cl$_2$ and the solution passed through silica gel, chromatographed on silica gel eluting with CH$_3$CO$_2$Et/C$_6$H$_{12}$ (1:1) and recrystallized from CH$_2$Cl$_2$/C$_6$H$_{12}$ to give the complex, as yellow needles: 35%; mp 177°–179° C. (dec); $^1$H NMR (CDCl$_3$) δ 1.15, 1.19 [2d, (CH'$_3$)$_2$C'H', J=6.6, 6.3 Hz, 12H], 1.29, 1.33 [2d, (CH$_3$)$_2$C$\underline{H}$O, J=6.6, 6.3 Hz, 12H], 3.58 (s, PyCH$_2$', 2H), 3.95 (d, PyC$\underline{H}_2$, J=8.3 Hz, 2H), 4.34 [t, (RO$_2$C)$_2$C$\underline{H}$, J=8.3 Hz, 1H] 4.97 [h, (CH$_3$)$_2$C$\underline{H}$O, J=6.6 Hz, 2H], 5.11 [h, (CH$_3$)$_2$C$\underline{H}$O, J=6.3 Hz, 2H], 7.36 (dd, 5-Py$\underline{H}$, J=3.7, 1.8 Hz, 1H), 7.50 (d, 5'-Py$\underline{H}$, J=7.8 Hz, 1H), 7.77 (d, 3'-Py$\underline{H}$, J=8.3 Hz, 1H), 7.91 (m, 3,4,4'-Py$\underline{H}$, 3H); IR (KBr) 2980, 1720, 1695, 1660, 1280, 1100 cm$^{-1}$; MS (m/e) 661 (M$^+$—35, 12) 496 (M$^+$—C$_3$H$_7$OPdCl, 40), 467 (M$^+$—C$_4$H$_8$O$_2$PdCl, 73), 349 (M$^+$—C$_{10}$H$_{14}$PdCl, 62), 313 (C$_{17}$H$_{17}$N$_2$O$_4$$^+$, 100), 264 (C$_{15}$H$_{12}$M$_2$O$_2$$^+$,74).

Anal. Calcd. for C$_{30}$H$_{39}$N$_2$O$_8$PdCl: C, 51.66; H, 5.64; N, 4.02. Found, 51.59; H, 5.49; N, 3.94.

EXAMPLE 11

Chloro[6,6'-Bis[1",1"-bis(tert-butoxycarbonyl)ethyl]-2,2'-dipyridine-Cl",N,N']Palladium(II)

The product was prepared according to Example 10 and chromatographed (ThLC) on silica gel with CH$_3$CO$_2$Et/C$_6$H$_{12}$ and recrystallized from CH$_3$CO$_2$Et/C$_6$H$_{12}$ (1:1) to give the complex, as yellow micro needles: 20%; mp 170°–172° C. (dec); $^1$H NMR (CDCl$_3$) δ 1.39 (s, OC(CH$_3$)$_3$, 18H), 1.52 (s, —OC(CH$_3$)$_3$, 18H), 3.54 (s, PyC$\underline{H}_2$, 2H), 3.94 (d, PyC$\underline{H}_2$, J=8.5 Hz, 2H), 4.29 (t, C$\underline{H}_2$CH(CO$_2$R)$_2$, J=7.3 Hz, 1H), 7.38 (dd, 5-Py$\underline{H}$, J=6.1, 2.4 Hz, 1H), 7.49 (d, 5'-Py$\underline{H}$, J=7.9 Hz, 1H), 7.72 (d, 3'-Py$\underline{H}$, J=7.9 Hz, 1H), 7.86 (m, 3,4,4'-Py$\underline{H}$, 3H); IR (neat) 2920, 1690 (C=O), 1560, 1270 cm$^{-1}$; MS (m/e) 254 (77), 253 (89), 209 (100), 91 (C$_6$H$_7$N$^+$, 71).

Anal. Calcd. for C$_{34}$H$_{47}$N$_2$O$_8$PdCl.H$_2$O: C, 52.93; H, 6.40; N, 3.63. Found: C, 52.78; H, 5.95; N, 3.95.

Attempts to form the second Pd—C bond were in prt successful, however, the bis-metallated product was never isolated in its pure state. All attempts failed to circumvent its apparent lability.

EXAMPLE 12

6,6'-Bis[1",1"-bis[(benzyloxycarbonyl)ethyl]-2,2'-dipyridine]Palladium(II)

The product was prepared according to the method of Example 8 and recrystallized from CH$_2$Cl$_2$/C$_6$H$_{12}$ to give the complex, as yellow micro needles: 50%; $^1$H NMR (CDCl$_3$) δ 4.03 (s, PyC$\underline{H}_2$, 4H), 5.10 (d, PhCH$_A$O, J=14 Hz, 4H), 5.50 (d, PhCH$_B$O, J=14 Hz, 4H), 7.28 (m, Ar$\underline{H}$, 20H), 7.39 (d, 5-Py$\underline{H}$, J=8.0 Hz, 2H), 7.68 (d, 3-Py$\underline{H}$, J=8.0 Hz, 2H), 7.88 (t, 4-Py$\underline{H}$, J=8.0 Hz, 2H); IR (neat) 2980, 1705 (C=O), 1590, 1145 cm$^{-1}$; MS (m/e) 108 (C$_7$H$_8$O$^+$, 51), 107 (C$_7$H$_7$O$^+$, 45), 91 (C$_7$H$_7$$^+$, 100), 79 (C$_5$H$_5$N$^+$, 65) 77 (C$_6$H$_5$$^+$, 42).

EXAMPLE 13

Di(2,2,2-trifluoroethyl)malonate

The ester was prepared according to the procedure described in Organic Synthesis, Coll. Vol. IV. Bp 78°–79° C.; $^1$H NMR δ 3.57 (s, CH$_2$(CO$_2$R)$_2$, 2H), 4.52 (dq, —C$\underline{H}_2$CF$_3$, J$_{H-F}$=8.0 Hz, 4H); IR (neat) 1760 (C=O), 1294 (—CF$_3$), 1180 (—CF$_3$) cm$^{-1}$; MS (m/e) 268 (M$^+$, 3), 169 (M$^+$—CF$_3$CH$_2$O, 100), 127 (CF$_3$CH$_2$OCO$^+$, 34), 83 (CF$_3$CH$_2$$^+$, 48), 69 (CF$_3$$^+$, 33);

EXAMPLE 14

6,6′-Bis[1″,1″-bis(carb-2″,2″, 2″-trifluoroethoxy)ethyl]-2,2′-dipyridine

The intermediate was prepared according to the method of Example 1 utilizing the ester of Example 13 to yield a white crystalline solid, which was chromatographed on silica gel (ThLC) eluting with $C_6H_{12}$/EtOH (90:10) and crystallized from $CH_2Cl_2/C_6H_{12}$: 90%; mp 94°–95° C.; $^1$H NMR δ 3.58 (d, Py-C$\underline{H}_2$, J=7.9 Hz, 4H), 4.34–4.58 (m, OC$\underline{H}_2$CF$_3$ and Py—C$\underline{H}$2e,uns/H/ , 10H), 7.20 (d, 5-Py$\underline{H}$, J=7.3 Hz, 2H), 7.72 (t, 4-Py$\underline{H}$, J=7.9 Hz, 2H), 8.22 (d, 3-Py$\underline{H}$, J=7.9 Hz, 2H); MS m/e 716 (M+, 1.5), 617 (M+—$C_2F_3H_2$, 1.0), 517 (M+—$C_4F_6$-$H_5O_2$, 10), 83 ($C_2F_3H_2^+$, 100).

EXAMPLE 15

6,6′-Bis[1″,1″-bis(carbo-2″,2″,2″-trifluoroethoxy)ethyl]-2,2′-dipyridine-Palladium(II)

The complex was prepared according to the method of Example 8 to yield the product, as yellow crystals: $^1$H NMR δ 3.99 (s, Py—C$\underline{H}_2$, 4H), 4.60 (m, —OC$\underline{H}_2$CF$_3$, 8H), 7.55 (d, 5-Py$\underline{H}$, J=7.9 Hz, 2H), 7.70 (d, 3-$\underline{P}$y$\underline{H}$, J=7.9 Hz, 2H), 7.98 (t, 4-Py$\underline{H}$, J=7.9 Hz, 2H).

EXAMPLE 16

Chloro[6,6′-bis[1″,1″-bis(carbo-2″,2″,2″-trifluoroethoxy(ethyl]-2,2′-dipyridine]Palladium(II)

This complex was prepared according to the method of Example 8 to yield the intermediate: $^1$H NMR δ 3.95 (s, PyC$\underline{H}_2$, 2H), 3.58 (d, PyC$\underline{H}_2$, J=7.9 Hz, 2H), 4.34–4.60 (m, OC$\underline{H}_2$CF$_3$, C$\underline{H}_2$C$\underline{H}$, 5H), 4.64 (m, OC$\underline{H}_2$CF$_3$, 4H), 7.20–8.22 (complex aromatic region). This intermediate was converted (85%) to the desired bis-Pd—C complex.

EXAMPLE 17

Di-(2,2-dimethyl-1,3-dioxolane-4-methylene)malonate

The ester was prepared according to the method of Example 13. Bp. 135°–136° C. (0.5 mm); $^1$H NMR δ 1.28 (s, (C$\underline{H}_3$)$_A$(CH$_3$)$_B$C, 6H), 1.34 (s, (CH$_3$)$_A$(C$\underline{H}$ $_3$)$_B$C, 6H), 3.39 (s, C$\underline{H}_2$(CO$_2$—)$_2$, 2H), 3.48–3.73 (m, O—CH-$_2$—C$\underline{H}$(O)CH$_2$—OC(CH$_3$)$_2$, 4H), 3.90–4.30 (m, O—C$\underline{H}$ $_2$—C$\underline{H}$(O)C$\underline{H}_2$OC(CH$_3$)$_2$, 6H); IR 1740 (C=O), 1382, 1370, 1075, 1050 cm$^{-1}$; MS m/e 317 (M+—CH$_3$, 100), 259 (M+—$C_3H_6O$, 30), 185 ($C_8H_9O_2^+$, 66), 143 ($C_6H_7O_4^+$, 69), 101 ($C_4H_5O_3^+$, 71), 43 ($C_3H_7^+$, 60);

EXAMPLE 18

6,6′-Bis[1″,1″-bis(carb-2″,2″-dimethyl-1″,3″-dioxolane-4″-methyleneoxy)ethyl]-2,2′-dipyridine The intermediate was prepared according to the procedure of Example 1 to yield an oil, which was chromatographed (ThLC) eluting with $CH_2Cl_2:C_6H_{12}:CH_3CO_2Et$ (60:20:20); 40%; $^1$H NMR δ 1.20 (s, (C$\underline{H}_3$)$_A$(CH$_3$)$_B$C, 12H), 1.27 (s, (CH$_3$)$_A$(C$\underline{H}_3$)$_B$C, 12H), 3.40 (d, Py—C$\underline{H}_2$, J=7.3 Hz, 4H), 3.48–3.60 (m, O—C$\underline{H}_2$CH(O)C$\underline{H}_2$ OC(CH$_3$)$_2$, 8H), 3.91–4.17 (m, O—CH$_2$—C$\underline{H}$(O)CH$_2$OC(CH$_3$)$_2$, 12H), 4.26 (t, Py—CH$_2$C$\underline{H}$, J=7.3 Hz, 2H), 7.09 (d, 5,5′-Py$\underline{H}$, J=7.3 Hz, 2H), 7.61 (t, 4-Py$\underline{H}$, J=7.8 Hz, 2H), 8.14 (d, 3-Py$\underline{H}$, J=7.8 Hz, 2H); IR (neat) 1745 (C=O), 1575, 1454, 1384, 1372 cm$^{-1}$; MS m/e 829 (M+—CH$_3$, 3), 117 ($C_8H_7N^+$, 56), 101 ($C_4H_5O_3^+$, 48), 43 ($C_3H_7^+$, 100).

EXAMPLE 19

6,6′-bis[1″,1″-bis(carb-2″,2″-dimethyl-1″,3″-dioxolane-4″-methyleneoxy)ethyl]-2,2′-dipyridine palladium(II)

The method of preparation was identical to that of Example 8 except that the product was isolated and the product of Example 18 was used as the starting material: $^1$H NMR δ 1.38, 1.39 (2s, (CH$_3$)$_2$C, 24H), 3.71 (m, PyC$\underline{H}_2$, CHC$\underline{H}_2$O, 12H), 4.20 (m, CO$_2$C$\underline{H}_2$CH, 12H), 7.50 (d, 5-Pyr$\underline{H}$, J=8.0 Hz, 2H), 7.80 (d, 3-$\overline{P}$yr$\underline{H}$, J=8.0 Hz, 2H), 8.00 (t, 4-Pyr$\underline{H}$, J=8.0 Hz, 2H).

EXAMPLE 20

Chloro[6,6′-bis[1″,1″-bis(carb-2″,2″-dimethyl-1″,3″-dioxolane-4″-methyleneoxy)ethyl]-2,2′-dipyridine]Palladium(II)

Method of preparation was the same as Example 8 except that the intermediate was isolated and the product of Example 18 was used as the starting material: low melting solid; $^1$H NMR δ 1.38, 1.39 (2s, (CH$_3$)$_2$C, 24H), 3.71 (m, PyC$\underline{H}_2$, CHC$\underline{H}_2$O, 12H), 4.20 (m, CO$_2$C$\underline{H}_2$CH, 12H), 7.32 (m, 5,5′-Py$\underline{H}$, 2H), 7.80 (m, 3,3′,4,4′-Py$\underline{H}$, 4H).

EXAMPLE 21

2,9-Bis[1″,1″-(bis(methoxycarbonyl)ethyl)]-1,10-phenanthroline

The intermediate was prepared as outlined for Example 1, except for the use of dimethyl malonate and 2,9-di(chloromethyl)-1-10-phenthroline: mp 120°–122° C.; $^1$H NMR (CDCl$_3$; 80 MHz) δ 3.75 [s, C$\underline{H}$(CO$_2$CH$_3$)$_2$, 12], 3.75(d, PyC$\underline{H}_2$, 4H), 4.66 (t, PyCH$_2$C$\underline{H}$, J=7.6 Hz, 2H), 7.51 (d, 3,8-$\overline{P}$y$\underline{H}$, J=8.6 Hz, 2H), 7.66 (s, 5,6-Ph$\underline{H}$, 2H), 8.10 (d, 4.7-Ph$\underline{H}$, J=8.6 Hz, 2H); MS (70 eV) m/e 469 (M+ +1,8), 468 (M+, 27), 437(22), 409(100), 345 (89), 233 (61), 59 (98).

Anal. Calcd. for $C_{24}H_{24}N_2O_8$: C, 61.57; H, 5.13; N, 5.98. Found: C, 61.21; H, 5.31; N, 5.77.

EXAMPLE 22

Chloro[2,9-Bis[1″,1″-(bis(methoxycarbonyl)ethyl)]-1,10-phenanthroline-Cl,N,N]Palladium(II)

The procedure of Example 10 was followed except that 2,9-bis[1″,1″-(bis(methoxycarbonyl)ethyl)]-1,10-phenanthroline was substituted for 6,6′-bis-[1″,1″-bis-(isopropoxycarbonyl)ethyl]-2,2′-dipyridine: mp 120°–122° C. (dec); $^1$H NMR (CDCl$_3$) δ 3.70 [s, —CH(CH$_2$CH$_3$)$_2$, 6H], 3.84 [s, Pd—C(CO$_2$CH$_3$), 6H],3.86 (s, $\overline{P}$yC$\underline{H}_2$, 2H), 4.11 (d, PyC$\underline{H}_2$, J=8.0 Hz, 2H), 4.39 (t, PyC$\underline{H}_2$CH, J=7.5 Hz, 1H), 7.65 (d, 8-Ph$\underline{H}$, J=6.5 Hz, 1H), 7.80 (d, 3-Ph$\underline{H}$, J=6.5 Hz, 1H), 7.89 (s, 5,6-Ph$\underline{H}$, 2H), 8.36 (d, 7-Ph$\underline{H}$, J=6.5 Hz, 1H), 8.43 (d, 4-Ph$\underline{H}$, J=6.5 Hz, 1H); MS(70 eV) m/e 466 (3), 436 (3), 435 (9), 434 (4), 422 (25), 407 (28), 375 (93), 349 (54), 317 (100), 44 (66).

Anal. Calcd. for $C_{24}H_{23}N_2O_8PdCl$: C, 47.24; H, 3.96; N, 4.59. Found: C, 47.11; H, 4.01; N, 4.52.

EXAMPLE 23

Chloro[2,9-Bis[1″,1″-(bis(isopropoxycarbonyl)ethyl)]1,10-phenanthroline-Cl,N,N]Palladium(II)

The procedure of Example 10 was followed except that 2,9-bis[1″,1″-(bis-(isopropoxycarbonyl)ethyl]-1,10-phenanthroline was substituted for 6,6′-bis[1″,1″-bis-(isopropoxy)ethyl]-2,2′-dipyridine: mp 88°–92° C.; $^1$H NMR (CDCl$_3$) δ 1.14, 1.19 [2d, (CO$_2$CH(C$\underline{H}_3$)$_2$, J=6.1, 6.1 Hz, 12H], 1.28, 1.35 [2d, Pd—C(CO$_2$CH(CH$_3$)$_2$)$_2$, J=6.7, 8.5 Hz, 12H], 3.81 (s, PhCH$_2$, 2H), 4.10 (d, PhCH$_2$, J=7.9 Hz, 2H), 4.43 [t, (RO$_2$C)$_2$CH, J=8.0 Hz, 1H], 4.98 [h, (CH$_3$)$_2$CHO, J=6.1 Hz, 2H], 5.13 [h, (CH$_3$)$_2$CHO, J=6.1 Hz, 2H], 7.67 (d, 8-PhH, J=8.5 Hz, 1H), 7.79 (d, 3-PhH, 8.5 Hz, 1H), 7.86 (s, 5,6-PhH, 2H), 8.31 (d, 7-PhH, J=7.9 Hz, 1H), 8.37 (d, 4-PhH, J=7.9 Hz, 1H); MS (70 eV) m/e 684 (2), 520 (22), 519 (22), 518 (18), 491 (26), 232 (68), 231 (72), 229 (89), 43 (100).

Anal. Calcd. for C$_{32}$H$_{39}$N$_2$O$_8$PdCl: C, 53.27; H, 5.41; N, 3.88. Found: C, 52.66; H, 5.63; N, 3.79.

EXAMPLE 24

1,2-Bis[3,3'-(bis(carbomethoxy)prop-1-oxy)]ethane

A mixture of dimethyl malonate (70 mmol), 1,2-bis-(2-iodoethoxy)ethane (20 mmol) and anhydrous K$_2$CO$_3$ (70 mmol) was stirred in acetonitrile (30 mL) at reflux for 72 hours. The heterogeneous mixture was filtered through celite, concentrated in vacuo and passed through a short silica column eluting with CH$_2$Cl$_2$. The solution was concentrated in vacuo yielding a colorless oil: $^1$H NMR (CDCl$_3$) δ 2.17 [dt, —CH$_2$CH(COR)$_2$, J=5.8, 2.1 Hz, 4H], 3.27 [td, —CH$_2$CH(CO$_2$R)$_2$, J=6.9, 2.8 Hz, 2H], 3.63 (m, —CH$_2$O, 8H), 3.74 (s, —OCH$_3$, 12H).

EXAMPLE 25

Bis-2-(6-methylpyridyl)ketone

To a solution of 2-methyl-6-bromopyridine (19 g, 0.11 mol) in THF (150 ml) cooled to −90° C. (pet. ether-liquid nitrogen) under argon, n-buLi (0.1 mol, 2.4M in hexane) was added dropwise. The resultant solution was stirred at −90° C. for 1 hour, then a solution of ethyl chloroformate (6 g, 0.55 mmol) in THF (15 ml) was added rapidly while still maintaining the temperature < −80° C. After stirring for 1.5 hours at −80° C., the reaction was quenched with MeOH (10 ml). The solvent was removed in vacuo and the residue extracted with CHCl$_3$, followed by washing with a NaHCO$_3$ solution. The combined organic extract was dried, concentrated, and column chromatographed eluting with C$_6$H$_{12}$/EtOAc (1:1) to give bis-2-(6-methylpyridyl)ketone, as colorless needles: 5.6 g (48%); mp 61° C.; bp 162°–166° C. (2.8 mm); R$_f$ 0.42; IR (CHCl$_3$) 1681 (C=O) cm$^{-1}$; $^1$H NMR (CDCl$_3$) δ 2.65 (s, CH$_3$, 6H), 7.35 (dd, 5-Py-H, J=7.7, 0.5 Hz, 2H), b 7.76 (t, 4-PyH, J=7.7 Hz, 2 H), 7.91 (dd, 3-PyH, J=7.7, 0.5 Hz, 2H); MS (70 eV) m/e 212 (77), 183 (100).

Anal. Calcd. for C$_{13}$H$_{12}$N$_2$O: C, 73.56; H, 5.70; N, 13.20. Found: C, 73.40; H, 5.85; N, 13.25

EXAMPLE 26

Bromination of Bis-2-(6-methylpryidyl)ketone

To a solution of above ketone (2.0 g, 9.45 mmol in anhydrous CCl$_4$ (200 ml) was added recrystallized (and in vacuo dried) N-bromosuccinimide (3.7 g, 20.8 mmol), then benzoyl peroxide (40 mg). The mixture was refluxed under illumination (100 W bulb) and a nitrogen atmosphere for 4 hours. After cooling and filtration, the filtrate was washed with a Na$_2$CO$_3$ solution, dried, and concentrated in vacuo to give a viscous residue, which was column chromatographed on silica gel eluting with EtOAc-C$_6$H$_{12}$ (1:1) to give the desired symmetrical titled dibromide, as off-white crystals: 580 mg (17%); mp 102°–103° C. (dec., CHCl$_3$—EtOH); R$_f$ 0.70; IR (CHCl$_3$) 1686 (C=O) cm$^{-1}$; $^1$H NMR (CDCl$_3$) δ 4.61 (s, CH$_2$, 4H), b 7.68 (dd, 5-PyH, J=7.7, 1.1 Hz, 2H), 7.91 (d, 4-PyH, J=7.7 Hz, 2H), 8.06 (dd, 3-PyH, J=7.7, 1.1 Hz, 2H); MS (70 eV) m/e 372 (1.0), 370 (1.4), 368 (1.0), 291 (100), 280 (83), 210 (28).

Anal. Calcd. for C$_{13}$H$_{10}$Br$_2$N$_2$O: C, 42.19; H, 2.72; N, 7.57. Found: C, 41.96; H, 2.80; N, 7.46.

EXAMPLE 27

Reaction of the Dibromide of Example 26 with Potassium Diethyl Malonate

To a stirred solution of the above dibromide (290 mg, 0.784 mmol) in anhydrous DMF (1 mL), diethyl malonate (600 μl, 640 mg, 4.0 mmol) and K$_2$CO$_3$ (300 mg, 2.2 mmol) were added. The suspension was stirred at 25° C. for 2 days. After filtration, the supernatant and CHCl$_3$ washing were combined, and then concentrated in vacuo maintaining temperatures below 45° C. The residue was dissolved in CHCl$_3$, washed with water, dried over MgSo$_4$, filtered, and concentrated to give a viscous residue, which was chromatographed (ThLC) on silica gel eluting with C$_6$H$_{12}$—EtOAc (1:1) to give the tetraester, as a pale yellow oil; 220 mg (53%); R$_f$ 0.5; IR (CHCl$_3$) 1743 (C=O), 1729 (C=O), 1687 (ketone) cm$^{-1}$; $^1$H NMR (CDCl$_3$) δ 1.19 (t, CH$_2$CH$_3$, J=7.1 Hz, 12H), 3.47 (d, PyCH$_2$, J=7.5 Hz, 4H), 4.07 (t, CHCH$_2$, J=7.5 Hz, 2H), 4.11 (m, CH$_2$CH$_3$, 8H), 7.41 (dd, 5-PyH, J=7.7, 1.2 Hz, 2H), 7.79 (t, 4-PyH, J=7.7 Hz, 2H), 7.89 (dd, 3-PyH, J=7.7, 1.2 Hz, 2H); MS (70 eV), m/e 528 (75), 483 (32), 455 (35), 437 (53), 363 (100).

Anal. Calcd. for C$_{27}$H$_{32}$O$_9$N$_2$: C, 61.36; H, 6.10; N, 5.30. Found: C, 60.79; H, 6.23; N, 5.04

EXAMPLE 28

Bis-Pd-C Complex of Tetraethyl Ester of Example 27

A freshly prepared NaOEt (0.7 mmol)-EtOH (1 ml) was added to a stirred, anhydrous THF solution of PdCl$_2$ (C$_6$H$_5$CN)$_2$ (110 mg, 0.29 mmol) and the above tetraester (158 mg, 0.30 mmol) under a nitrogen atmosphere at 25° C. After 12 hours, the solvent was removed in vacuo. The residue was extracted with CH$_2$Cl$_2$ and after removal of the solvent, the concentrate was chromatographed (ThLC) on silica gel eluting with EtOAc—EtOH (10:1) to give the desired bis-complex, as an orange-yellow microcrystals: 15 mg (8%); mp 92°–94° C. (dec); R$_f$ 0.26; IR (CHCl$_3$) 1728 (C=O), 1674 (ketone) cm$^{-1}$; NMR (CDCl$_3$) δ 1.14 (t, CH$_2$CH$_3$, J=7.1 Hz, 12H), 3.64 (s, PyCH$_2$, 4H), 4.08 (m, OCH$_2$CH$_3$, 8H), 7.77 (d, 5-PyH, J=7.8 Hz, 2H), 8.03 (dd, 4-PyH, J=7.8, 7.8 Hz, 2H), 8.18 (d, 3-PyH, J=7.8 Hz, 2H), MS (70 eV) m/e 634 (3.6), 632 (4.1), 630 (3.1), 104 (100).

Anal. Calcd. for C$_{27}$H$_{30}$N$_2$O$_9$Pd: C, 51.24; H, 4.78; N, 4.43. Found: C, 50.95; H, 4.65; N, 4.21.

EXAMPLE 29

Bis-Pd-C-Complex of Tetramethyl Ester of Compound of Example 27

The tetramethyl ester was prepared by the above procedure then complexed via the metallation procedure of Example 28; 10%; $^1$H NMR δ 3.76 (s, OCH$_3$, 12H), 3.65 (s, PyCH$_2$, 4H), 7.75 (d, 5-PyH, J=7.8 Hz, 2H), 8.03 (dd, 4-PyH, 2H), 8.18 (d, 3-PyH, J=7.8 Hz, 2H).

EXAMPLE 30

Reaction of the Dibromoketone of Example 26 with Acetylacetone

A suspension of dibromide (150 mg, 0.41 mmol), acetylacetone (205 mg, 2.05 mmol), and $K_2CO_3$ (100 mg, 0.72 mmol) in anhydrous DMF (300 μL) was stirred at 25° C. for 2 days. After the removal of the solvent in vacuo, the $CHCl_3$ extract was chromatographed (ThLC) on silica gel eluting with EtOAc—$C_6H_{12}$ (1:1) to give the tetraketone, as a pale yellow solid: 78 mg (47%); mp 90°–92° C.; $R_f$ 0.31; IR ($CHCl_3$) 1728 (C=O) cm$^{-1}$; $^1$H NMR (very complicated due to keto-enol tautomerization); MS (70 eV) m/e 408 (5.5), 393 (6), 365 (23), 323 (100).

Anal. Calcd. for $C_{23}H_{24}N_2O_5$: C, 67.63; H, 5.92; N, 6.86. Found: C, 67.58; H, 5.90; N, 6.85.

EXAMPLE 31

Bis-Pd-C-Complex of the Bis-acetylacetone Ligand of Example 30

The tetraketone was complexed with $PdCl_2$, or comparable Pd(II) precursor, in the presence of $K_2CO_3$ (Example 8) to give the bis-complex, as yellow needles: 14%, $^1$H NMR (CDCl$_3$) δ 3.95 (s, PyC$\underline{H}_2$); 7.40 (d, 5-PyH, J=8.0 Hz, 2H), 7.70 (d, 3-Py$\underline{H}$, J=8.0 Hz, 2H), 7.88 (t, J=8 Hz, 2H).

EXAMPLE 32

6-[2,2-Bis(ethoxycarbonyl)ethyl]-2,2′-dipyridines General Procedure

A mixture of diethyl malonate (4.0 g, 25 mmol), 6-bromomethyl-2,2′-dipyridine [Newkome, Gupta, Fronczek, Inorg. Chem. 22, 171 (1983)] or 6-chloromethyl-6′-methyl-2,2′-dipyridine [Newkome et al., J. Org. Chem. 47, 4116 (1982)] and $K_2CO_3$ (2.5 g) in DMF (50 mL) was stirred for 20 hours at 25° C. The mixture was filtered, concentrated in vacuo, and chromatographed (ThLC) on silica gel eluting with pet. ether (bp 40°-60° C.)-ether (3:2) to afford the following bis-esters:

(a) 6-[2,2′-Bis(ethoxycarbonyl)ethyl]-2,2′-dipyridine: as an oil: bp 127°–128° C. (0.6 mm); 94%; $^1$H NMR δ (CDCl$_3$) δ 1.22 (t, —CH$_2$C$\underline{H}_3$, 6H, J=7.3 Hz), 3.52 (d, PyC$\underline{H}_2$, 2H, J=7.3 Hz), 3.85 (t, C$\underline{H}$(CH$_2$CO$_2$Et)$_2$, 1H J=7.3 Hz], 4.21 (m, C$\underline{H}_2$CH$_3$, 4H), 7.20 (d, 5-Py$\underline{H}$, 1H, J=7.9 Hz), 7.26 (dd, 5′-Py$\underline{H}$, 1H, J$_{4',5'}$=7.9 Hz, J$_{5',6'}$=4.3 Hz), 7.70 (t, 4′-Py$\underline{H}$, 1H, J=7.9 Hz), 7.78 (t, 4-Py$\underline{H}$, 1H, J=7.9 Hz), 8.27 (d, 3-Py$\underline{H}$, 1H, J=7.9 Hz), 8.45 (d, 3′-Py$\underline{H}$, 1H, J=7.9 Hz), 8.64 (d, 6′-Py$\underline{H}$, 1H, J=4.3 Hz); IR (neat) 2980, 1730 (C=O), 1425, 1260 cm$^{-1}$; MS (70 eV) m/e 328 (M$^+$, 27), 255 (M$^+$—CO$_2$Et, 83), 209 (M$^+$—C$_5$H$_{11}$O$_3$, 100), 183 (M$^+$—C$_6$H$_9$O$_4$, 75).

Anal. Calcd. for $C_{18}H_{20}N_2O_4$: C, 65.84; H, 6.14; N, 8.53. Found: C, 65.72; H, 5.97; N, 8.49.

(b) 6-[2,2-Bis(carbethoxy)ethyl]-6′-methyl-2,2′-dipyridine, as an oil: bp 146°–148° C. (1.3 mm), 91%; $^1$H NMR (CDCl$_3$) δ 1.19 (t, —CH$_2$C$\underline{H}_3$, 6H, J=7.3 Hz, 2.55 (s, PyC$\underline{H}_3$, 3H), 3.50 (d, PyC$\underline{H}_2$, 2H, J=7.3 Hz), 4.19 (m, C$\underline{H}_2$CH$_3$, 4H), 4.30 [t, C$\underline{H}$(CO$_2$Et)$_2$, 1H, J=7.3 Hz], 7.07 (d, 5-Py$\underline{H}$, 1H, J=7.3 Hz), 7.14 (d, 5′-Py$\underline{H}$, 1H, J=7.3 Hz), 7.62 (t, 4-Py$\underline{H}$, 1H, J=7.3 Hz), 7.64 (t, 4′-PyH1H, J=7.3 Hz), 8.24 (d, 3-Py$\underline{H}$, 1H, J=7.3 Hz), 8.28 (d, 3′-Py$\underline{H}$, 1H, J=7.3 Hz); IR (neat) 2980, 1730 (C=O), 1435, 1260 cm$^{-1}$; MS (70 eV) m/e 342 (M$^+$, 25) 297 (M$^+$—OEt, 13), 269 (M$^+$—CO$_2$Et, φ), 197 (M$^+$—C$_6$H$_9$O$_4$, 63)

Anal. Calcd. for $C_{10}H_{22}N_2O_4$: C, 66.65; H, 6.48; N, 8.18. Found: C, 66.36; H, 6.54; N, 8.02.

EXAMPLE 33

Preparation of cis-Dipyridine Palladium Complexes

A mixture of $PdCl_2$ (1.0 eq.) and the above 6-[2,2-bis-(ethoxycarbonyl)ethyl]-2,2′-dipyridines (1.0 eg.) in anhydrous $CH_3CN$ (50 mL) was stirred at 25° C. for 1 hour under a nitrogen atmosphere. Anhydrous $K_2CO_3$ (3.0 eq.) was added and the reaction mixture stirred for an additional 24 hours. The heterogeneous mixture was filtered through celite and concentrated in vacuo to give the crude product, which was chromatographed (ThLC on silica gel) and recrystallized from MeOH:

(a) Chloro[6-(2,2-bis(ethoxycarbonyl)ethyl)-2,2′-dipyridine]Palladium(II), as yellow needles: mp 183°–186° C. (dec.); 60%; $^1$H NMR (CDCl$_3$) δ 1.32 (t, CH$_2$C$\underline{H}_3$, 6H, J=7.3 Hz), 3.83 (s, PyC$\underline{H}_2$, 2H), 4.27 (m, C$\underline{H}_2$CH$_3$, J=7.3 Hz, 4H), 7.44 (d, 5,5′-Py$\underline{H}$, 2H, J=5.5 Hz), 7.84 (t, 4′-Py$\underline{H}$, 1H, J=5.5 Hz), 7.93 (t, 4-Py$\underline{H}$, 1H, J=5.5 Hz), 8.02 (d, 3,3′-Py$\underline{H}$, 2H, J=5.5 Hz), 8.81 (d, 6′-Py$\underline{H}$, 1H, J=5.5 Hz); IR (CsI) 2985, 1700 (C=O), 1480, 1270 cm$^{-1}$; MS (70 eV) m/e 411 [(M$^+$+1)-2Et, 2], 281 (M$^+$—C$_2$H$_6$OPdCl, 25), 255 (M$^+$—C$_3$H$_4$O$_2$PdCl, 36), 236 (M$^+$—C$_4$H$_{11}$O$_2$PdCl, 100), 209 (M$^+$—C$_5$H$_{10}$O$_3$PdCl, 53).

Anal. Calcd. for $C_{18}H_{19}N_2O_4PdCl$: C, 46.08; H, 4.08; N, 5.97. Found: C, 45.97; H, 4.38; N, 5.49.

(b) Chloro[2,2-bis(ethoxycarbonyl)ethyl-6′-methyl-2,2′-dipyridine]Palladium(II), as yellow needles: mp 219°–221° C. (dec.); 82%; $^1$H NMR (CDCl$_3$) δ 1.29 (t, CH$_2$C$\underline{H}_3$, 6H), J=7.3 Hz), 2.98 (s, PyC$\underline{H}_3$, 3H), 3.62 (s, PyC$\underline{H}_2$, 2H), 4.25 (m, C$\underline{H}_2$CH$_3$, 4H), 7.33 (dd, 5′-Py$\underline{H}$, 1H, J$_{4',5'}$=7.4 Hz, J$_{3',5'}$=1.8 Hz), 7.50 (d, 5-Py$\underline{H}$, 1H), 7.75 (2d, 3-Py$\underline{H}$, 1H, J=7.8 Hz, 3′-Py$\underline{H}$, 1H, J=7.4 Hz), 7.88 (t, 4′-Py$\underline{H}$, 1H, J=7.4 Hz), 7.92 (t, 4-Py$\underline{H}$, 1H, J=7.8 Hz); IR (CsI) 2980, 1705 (C=O), 1440, 1225 cm$^{-1}$; MS (70 eV) m/e 484 [M$^+$($^{37}$Cl), 1] 482 [M$^+$($^{35}$Cl), 1], 296 [M$^+$—C$_2$H$_5$OPdCl, 37], 250 [M$^+$—C$_5$H$_{11}$O$_2$PdCl, 100], 222 [M$^+$—CHOPdCl, 48].

Anal. Calcd. for $C_{19}H_{21}N_2O_4PdCl$: C, 47.22; H, 4.38; N, 5.80. Found: C, 46.94; H, 4.70; N, 5.74.

EXAMPLE 34

6,6′-Bis[1″,1″,2″,2″-tetrakis(methoxycarbonyl)propyl]-2,2′-dipyridine

This ligand was prepared according to the method of Example 1 except that 1,1,2,2-(tetramethoxycarbonyl)ethane was used in place of dimethyl malonate, to yield a crystalline solid. $^1$H NMR (CDCl$_3$) δ 3.73 (s, OMe, 24H), 3.77 (s, PyC$\underline{H}_2$, 4H), 4.56 [s, C$\underline{H}$(CO$_2$Me)$_2$, 2H], 7.17 (dd, 5-Py$\underline{H}$, J=7.6, 1.0 Hz, 2H), 7.75 (t, 4-Py$\underline{H}$, J=7.6 Hz, 2H), 8.18 (dd, 3-Py$\underline{H}$, J=7.6, 1.0 Hz, 2H).

EXAMPLE 35

Chloro[6,6′-Bis[1″,1″,2″,2″-tetrakis(methoxycarbonyl)-propyl]-2,2′-dipyridine]Palladium(II)

Method of preparation used the product of Example 34 and the procedures outlined in Example 8. $^1$H NMR (s, PdC(CO$_2$Me)$_2$, 6H), 3.72 (s, C(CO$_2$Me)$_2$, 6H), 3.75 (s, HC(CO$_2$Me$_2$)$_2$, 6H), 3.76 (s, C(CO$_2$$\overline{Me}$)$_2$, 6H), 4.00 (s, PyC$\underline{H}_2$, 2H), 4.32 (s, C$\underline{H}$(CO$_2$Me)$_2$, 1H), 4.46 (s, PyC$\underline{H}_2$, 2H), 7.33 (dd, 5′-Py$\underline{H}$, J=6.0, 3.0 Hz, 1H), 7.64

(dd, 5-PyH, J=5.0, 1.0 Hz, 1H), 7.92 (m, 3,3',4,4'-PyH, 4H).

The active anti-tumor drugs comprising first- and second-generation platinum coordination complexes possess common features of square-planar geometry and cis anionic leaving groups of intermediate lability [Leh et al, *J Pharmaceut. Sci.*, 65, 136 (1976)]. In addition, complexes of octahedral geometry, in which the cis configuration of leaving groups was maintained, have also been reported to be active, both in vivo and in vitro [Mong et al, *Cancer Res.* 40, 3318 (1980)]. Palladium analogs of the active platinum(II) complexes were originally found to be marginally cytotoxic [Cleare et al, *Bioinorg. Chem.* 2, 187 (1973)]; however, recent studies identified some palladium(II) complexes as having antibacterial, antiviral and very slight anti-cancer agents [Graham et al, *J. Inorg. Nucl. Chem.*, 41, 1245 (1979)].

Lesions in cellular DNA have been cited as the cytotoxic event in anti-tumor therapy with the known heavy metal complexes [Harder et al, *Int. J. Cancer*, 6, 207 (1979)]. A convenient substrate for determining these DNA lesions in vitro is supercoiled DNA. For example, the parent platinum complex, cis-diamminedichloroplatinum(II) [cis-Pt(II)], has been found to induce unwinding of phage PMs, DNA, followed by rewinding or denaturation [Mong et al, *Cancer Res.*, 40, 3313 (1980)]. The production of interstrand cross-links [Deutsch et al, *Biochem, Biophys. Res. Commun.*, 97, 1220 (1980)] has also been identified using phage PM2 DNA as a substrate. Furthermore, platinum and palladium complexes having planar aromatic ligands bind to DNA by an intercalative mechanism [Howe-Grant, et al, *Biochemistry*, 15, 4339 (1976)]. Platinum(IV) complexes produce strand breakage with covalently closed circular PM2 DNA [Mong et al, *Cancer Res.*, 40, 3318 (1980)].

The results of the tests and experiments set forth hereinbelow indicate that the cis-palladium complexes of the present invention produced strand-breaks in phage PM2 DNA. The corresponding trans-isomers failed to produce any detectable damage [Newkome et al, *J. Am. Chem. Soc.*, 102, 4511 (1980)]. Significant levels of binding between the complex and DNA were detected by several techniques including filtration through nitrocellulose, buoyant density determination, and nick translation with *Escherichia coli* DNA polymerase I.

EXAMPLE 36

Stock ligands of ligands and complexes were made by dissolving crystalline material in either ethanol or dimethylsulfoxide. These solutions were diluted immediately before use with dH$_2$O. Schleicher and Schuell-type BA-85 nitrocellulose filters were utilized in determining filter-binding events.

The preparation of phage PM2 [3H] DNA is described in Juhnlein et al, *Mutation Res.*, 64, 167 (1979) except that the multiplicity of infection was 2. The resulting thymidine-labeled DNA had a specific activity of 156 cpm/fmol of DNA molecules.

Analysis of Filter-Binding Events (FBE): Reaction mixtures (0.05 mL) contained 50-70 fmol of PM2 [3H] DNA molecules, 25 mM Tris-HCl (pH 7.5), 10 mM MgCl$_2$, and organopalladium complex. Incubations were at 37° C. for 5 min. The reaction was terminated by addition of 0.15 mL of 0.01% sodium dodecyl sulfate, 2.5 mM EDTA (pH 7.5). Single-strand breaks were analyzed as described in Kuhnlein et al, [*Mutation Res.*, 64, 167 (1979)]. Associative binding of organopalladium complexes to DNA was determined similarly except that 0.3 mL dH$_2$O was added instead of alkali and neutralizing acid. A filter binding event is that amount of DNA retained on intracellulose filters in the presence of the organopalladium complex and is presumed to represent the formation of a complex between DNA and 1. No determination was made, however, on the number of binding events necessary for the filter to retain a DNA molecule.

Buoyant Density Determination: Incubation conditions were as described above for analysis of filter binding events. After termination of the reaction, 260 fmol of unlabeled PM2 DNA molecules were added as carrier. Polyallomer centrifuge tubes were filled to 3.0 ml with the reaction mixture suspended in CsCl of density 1.70 g/ml. The tubes were topped with mineral oil and centrifuged at 400,000 rpm for 24 hours at 24° C. in a SW 50.1 rotor. Fractions (0.08 ml) were collected from the bottom of the tube and the refractive index determined immediately with an Abbe Refractometer. Each aliquot was diluted with 0.3 ml dH$_2$O and 3.5 ml aqueous fluor. The results are expressed as percentage of recovered counts per fraction. Average recovery of radioactivity from the gradient was 71%.

DNA Synthesis: Reaction mixtures (0.05 ml) contained 70 mM potassium phosphate (pH 7.5), 25 mM Tris-HCL (pH 7.5), 10 mM MgCl$_2$, 100 $\mu$Meach dTTP, dCTP, dGTP, 1.2 $\mu$M [8-3H] dATP (17 Ci/mmol), 80 fmol PM2 DNA molecules, 0115 unit *E. Coli* DNA polymerase 1 and 1. Following incubation of 1 with DNA in the standard filter binding assay, the polymerase in 70 mM potassium phosphate (pH 7.5) and labeled dNTPs were added and incubated at 37° C. for 1 hour. The reaction was terminated by placing on ice for 15 min. and adding 0.15 ml 10% TCA. The acid-insoluble product was collected on Whatman GF/C filters soaked in 10% TCA. Each filter was washed with 10% TCA (30 ml), dried and counted to determine radioactivity.

It is generally regarded that anti-tumor agents, such as cis-dichlorodiamine Pt(II), exerts its anti-tumor properties by acting on DNA, resulting in an eventual interruption of DNA replication [Roberts et al, *Prog. Nucleic. Acid. Res. Mol. Biol.*, 22, 71–133 (1978)]. As shown in Table I, individual reactions in which DNA is exposed to increasing amounts of complex eventually results in the inhibition of DNA synthesis catalyzed by *E. Coli* DNA polymerase 1. An absolute criteria for detecting DNA synthesis is that the DNA substrate must contain a 3'OH primer terminius [Kelly et al, *J. Biol. Chem.*, 245, 39 (1970)]. The initial increase in DNA synthesis seen in Table I is possibly a result of the complex introducing additional nicks into a DNA substrate that already contains a certain proportion of naturally occurring nicks. On the other hand, it could be that the complex influences the secondary structure of the template primer so as to initially stimulate DNA synthesis. It is clear from Table I that at high concentrations of the complex, DNA synthesis is inhibited. This is particularly evident where values of [3H] dATP incorporated per DNA molecule fall below that observed for the untreated DNA substrate. It thus appears that high concentrations of the complex are creating a DNA adduct, possibly through its binding to DNA, that is refractive to DNA synthesis. Indeed, a significant shift in buoyant density was observed for PM2 DNA reacted with the complex (40 μM) and subsequently sedimented in CsCl gradients. The refractive index of the fraction representing maximal recovery of radioactivity was used to calculate band density [Vinograd et al, *Prog. Org. Chem. Nat. Prod., XX,* 417 (1962)]. The calculated density of untreated PM1 DNA, 1.685 g/ml, is close to the value of 1.694 g/ml reported as the density of PM2 Form 1 DNA [Bauer et al, *Biochemistry,* 17, 1060 (1978)]. The band representing PM2 DNA treated with complex resulted in a buoyant density of 1.720 g/ml, or an increment of 35 mg/ml. The gradient profiles failed to show any detectable conversion to Form II DNA.

Incubations containing DNA treated with complex are passed over nitrocellulose filters, either with or without prior treatment with alkali. DNA that remains bound to nitrocellulose, in the absence of alkali treatment, usually is a measure of some specific protein: DNA interaction [Deutsch et al, *Proc. Natl. Acad. Sci., U.S.A.,* 76, 141-144 (1979)], or a reflection of DNA containing adducts generated by some chemical [Demple et al, *J. Biol. Chem.,* 257, 2848–2855 (1982)]. DNA that is trapped on nitrocellulose filters after exposure to alkali usually reflects DNA that contains nicks. DNA treated with complex sticks to nitrocellulose filters regardless of pretreatment with alkali. However, PM2 DNA reacted with the complex and treated with alkali shows an evident increase in binding events. In light of results obtained from CsCl gradients, it appears that the large degree of "nicking" detected by alkali treatment and filtration are actually artifacts peculiar to this organometallic complex.

The fact that the complex interacts with DNA so as to change its buoyant density and its ability to support DNA synthesis is clear evidence of its anti-tumor activity.

TABLE I

| Nick Translation on PM2 DNA Treated with Complex of Example | |
|---|---|
| Concentration of Complex μM | [$^3$H] dATP incorporated per DNA molecule |
| 0 | 5 |
| 0.1 | 10 |
| 0.2 | 23 |
| 0.5 | 9 |
| 1.0 | 6 |
| 4.0 | 4 |
| 10.0 | 2 |
| 20.0 | 1 |

I claim:

1. A coordination complex of palladium (II) having the formula:

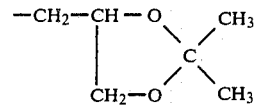

(VII)

wherein: $R_1$, $R_2$, $R_3$, $R_4$ are lower alkyl groups, fluoro substituted lower alkyl groups, ar(lower)alkyl, or

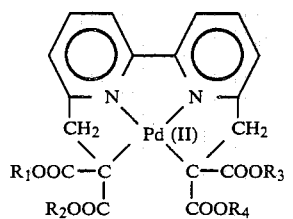

2. A complex of claim 1 wherein $R_1$, $R_2$, $R_3$, and $R_4$ are lower alkyl groups.

3. A complex of claim 1 wherein $R_1$, $R_2$, $R_3$, and $R_4$ are fluoro-substituted lower alkyl groups.

4. The complex of claim 1 wherein $R_1$, $R_2$, $R_3$, and $R_4$ are methyl.

5. The complex of claim 1 wherein $R_1$, $R_2$, $R_3$, and $R_4$ are ethyl.

6. The complex of claim 1 wherein $R_1$, $R_2$, $R_3$, and $R_4$ are isopropyl.

7. The complex of claim 1 wherein $R_1$, $R_2$, $R_3$, and $R_4$ are t-butyl.

8. The complex of claim 1 wherein $R_1$, $R_2$, $R_3$, and $R_4$ are $CF_3CH_2$—.

9. A complex of claim 7 wherein $R_1$, $R_2$, $R_3$ and $R_4$ are ar(lower)alkyl groups.

10. A complex of claim 7 wherein $R_1$, $R_2$, $R_3$ and $R_4$ are

11. The complex of claim 7 wherein $R_1$, $R_2$, $R_3$ and $R_4$ are benzyl.

12. A pharmaceutical composition in unit dosage form adapted for the treatment of animal tumor cells sensitive to a complex of palladium (II) comprising a pharmaceutically acceptable carrier and an anti-tumor effective amount of a coordination complex of palladium (II) having the formula:

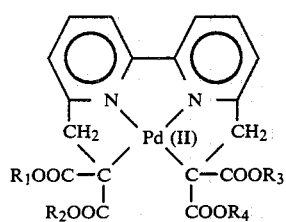

(VII)

wherein: $R_1$, $R_2$, $R_3$, $R_4$ are lower alkyl groups, fluoro substituted lower alkyl groups, ar(lower)alkyl, or

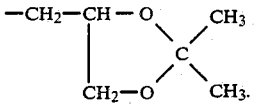

13. The composition of claim 12 wherein $R_1$, $R_2$, $R_3$ and $R_4$ are lower alkyl groups.

14. The composition of claim 12 wherein $R_1$, $R_2$, $R_3$ and $R_4$ are fluoro-substituted lower alkyl groups.

15. The composition of claim 12 wherein $R_1$, $R_2$, $R_3$ and $R_4$ are methyl.

16. The composition of claim 12 wherein $R_1$, $R_2$, $R_3$ and $R_4$ are ethyl.

17. The composition of claim 12 wherein $R_1$, $R_2$, $R_3$ and $R_4$ are isopropyl.

18. The composition of claim 12 wherein $R_1$, $R_2$, $R_3$ and $R_4$ are t-butyl.

19. The composition of claim 12 wherein $R_1$, $R_2$, $R_3$ and $R_4$ are $CF_3CH_2$.

20. The composition of claim 12 wherein $R_1$, $R_2$, $R_3$ and $R_4$ are ar(lower)alkyl groups.
21. The composition of claim 12 wherein $R_1$, $R_2$, $R_3$ and $R_4$ are
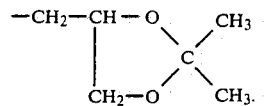
22. The composition of claim 12 wherein $R_1$, $R_2$, $R_3$ and $R_4$ are benzyl.
* * * * *

UNITED STATES PATENT AND TRADEMARK OFFICE
CERTIFICATE OF CORRECTION

PATENT NO. : 4,598,073
DATED : July 1, 1986
INVENTOR(S) : George R. Newkome

Page 1 of 3

It is certified that error appears in the above-identified patent and that said Letters Patent is hereby corrected as shown below:

Column 3, lines 20-25: Delete second formula

Column 3, line 62: "inraperitoneal" should read as --intraperitoneal--

Column 9, line 25: "$^1$N NMR" should read as --$^1$H NMR--

Column 10, lines 39-40: "were in prt successful" should read as --were in part successful--

Column 11, line 12: "(m, OC$\underline{H}_2$CF$_3$ and Py-CH$_{2e'}$ uns/H/ , 10H)" should read as --(m, OC$\underline{H}_2$CF$_3$ and Py-CH$_2$C$\underline{H}$, 10H)--

Column 11, line 48: "cm$^{-i}$" should read as --cm$^{-1}$--

Column 13, line 68: "4H), b 7.68" should read as --4H), 7.68--

UNITED STATES PATENT AND TRADEMARK OFFICE
CERTIFICATE OF CORRECTION

PATENT NO. : 4,598,073
DATED : July 1, 1986
INVENTOR(S) : George R. Newkome

It is certified that error appears in the above-identified patent and that said Letters Patent is hereby corrected as shown below:

Column 16, line 1: "$M^+-CO_eEt, \underline{100})$" should read as --$(M+ -CO_2Et, \underline{100})$--

Column 16, line 3: "$C_{10}$" should read as --$C_{19}$--

Column 18, line 32: "polymerase 1 and 1" should read as --polymerase 1 and $\underline{1}$--

Column 20, line 22, Claim 9: in all occurences change "7" to --1--

Column 20, line 24, Claim 10: in all occurences change "7" to --1--

Column 20, line 24, Claim 10: after "are" insert the formula

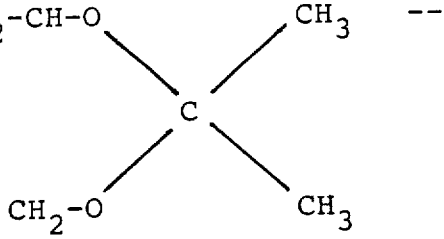

UNITED STATES PATENT AND TRADEMARK OFFICE
CERTIFICATE OF CORRECTION

PATENT NO. : 4,598,073

DATED : July 1, 1986

INVENTOR(S) : George R. Newkome

It is certified that error appears in the above-identified patent and that said Letters Patent is hereby corrected as shown below:

Column 20, line 26, Claim 11: in all occurences change "7" to --1--

Signed and Sealed this

Fifteenth Day of March, 1988

*Attest:*

DONALD J. QUIGG

*Attesting Officer*      *Commissioner of Patents and Trademarks*